United States Patent
Bae et al.

(10) Patent No.: US 9,482,948 B2
(45) Date of Patent: Nov. 1, 2016

(54) PHOTORESIST COMPOSITIONS AND METHODS OF FORMING PHOTOLITHOGRAPHIC PATTERNS

(71) Applicant: Rohm and Haas Electronic Materials LLC, Marlborough, MA (US)

(72) Inventors: Young Cheol Bae, Weston, MA (US); Deyan Wang, Hudson, MA (US); Thomas Cardolaccia, Newton, MA (US); Seokho Kang, Sturbridge, MA (US); Rosemary Bell, Wayland, MA (US)

(73) Assignee: Rohm and Haas Electronic Materials LLC, Malborough, MA (US)

( * ) Notice: Subject to any disclaimer, the term of this patent is extended or adjusted under 35 U.S.C. 154(b) by 0 days.

(21) Appl. No.: 14/919,822

(22) Filed: Oct. 22, 2015

(65) Prior Publication Data
US 2016/0109800 A1   Apr. 21, 2016

Related U.S. Application Data

(63) Continuation of application No. 13/149,573, filed on May 31, 2011, now Pat. No. 9,188,864.

(51) Int. Cl.
*G03F 7/004*    (2006.01)
*G03F 7/40*    (2006.01)
(Continued)

(52) U.S. Cl.
CPC ............. *G03F 7/0382* (2013.01); *C07C 69/54* (2013.01); *G03F 7/0392* (2013.01);
(Continued)

(58) Field of Classification Search
CPC .... G03F 7/004; G03F 7/0045; G03F 7/2041; G03F 7/0397; G03F 7/11; G03F 7/325; G03F 7/40; G03F 7/09; G03F 7/091; H01L 21/0276; H01L 21/312; H01L 21/0274; H01L 21/0275; H01L 21/332; H01L 21/32139; C07C 2103/74; C07C 69/54; C08F 2220/283; C08F 220/302
USPC ...... 430/270.1, 271.1, 273.1, 322, 325, 330, 430/331, 434, 435, 436, 913, 945
See application file for complete search history.

(56) References Cited

U.S. PATENT DOCUMENTS 6,737,212 B1   5/2004   Takahashi
6,790,579 B1   9/2004   Goodall et al.
(Continued)

FOREIGN PATENT DOCUMENTS

EP   1739483 A2   1/2007
JP   2006071889 A   3/2006
(Continued)

OTHER PUBLICATIONS

Search Report for corresponding Taiwan Application No. 100118824.
(Continued)

*Primary Examiner* — Amanda C Walke
(74) *Attorney, Agent, or Firm* — Jonathan D. Baskin

(57) ABSTRACT

Provided are photoresist compositions useful in forming photolithographic patterns by a negative tone development process. Also provided are methods of forming photolithographic patterns by a negative tone development process and substrates coated with the photoresist compositions. The compositions, methods and coated substrates find particular applicability in the manufacture of semiconductor devices.

11 Claims, 1 Drawing Sheet

Figure 1A:
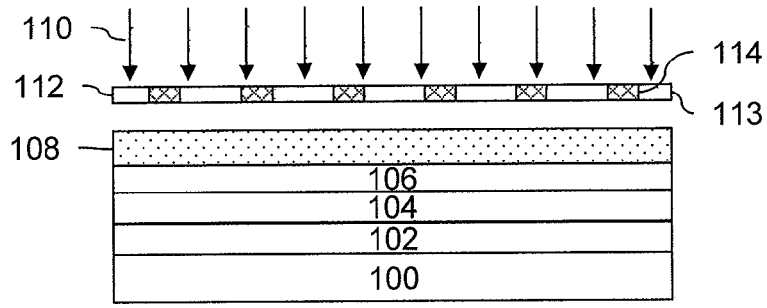

(51) Int. Cl.
| | |
|---|---|
| *G03F 7/038* | (2006.01) |
| *H01L 21/027* | (2006.01) |
| *C07C 69/54* | (2006.01) |
| *G03F 7/039* | (2006.01) |
| *G03F 7/11* | (2006.01) |
| *G03F 7/20* | (2006.01) |
| *G03F 7/32* | (2006.01) |
| *G03F 7/16* | (2006.01) |
| *C08F 220/28* | (2006.01) |

(52) U.S. Cl.
CPC .......... *G03F 7/0395* (2013.01); *G03F 7/0397* (2013.01); *G03F 7/11* (2013.01); *G03F 7/16* (2013.01); *G03F 7/20* (2013.01); *G03F 7/2041* (2013.01); *G03F 7/32* (2013.01); *G03F 7/325* (2013.01); *G03F 7/40* (2013.01); *H01L 21/0274* (2013.01); *H01L 21/0276* (2013.01); *C07C 2103/74* (2013.01); *C08F 2220/283* (2013.01)

(56) References Cited

U.S. PATENT DOCUMENTS

| | | | |
|---|---|---|---|
| 7,700,560 | B2 | 4/2010 | Creighton et al. |
| 7,776,506 | B2 | 8/2010 | Wang et al. |
| 7,998,655 | B2 | 8/2011 | Tsubaki |
| 8,017,298 | B2 | 9/2011 | Tsubaki |
| 8,257,902 | B2 | 9/2012 | Wang et al. |
| 2003/0087194 | A1 | 5/2003 | Endo et al. |
| 2006/0051702 | A1 | 3/2006 | Endo et al. |
| 2006/0246373 | A1 | 11/2006 | Wang |
| 2007/0134916 | A1 | 6/2007 | Iwabuchi et al. |
| 2009/0042147 | A1 | 2/2009 | Tsubaki |
| 2010/0015554 | A1 | 1/2010 | Saegusa et al. |
| 2010/0040972 | A1 | 2/2010 | Tarutani et al. |
| 2010/0233626 | A1 | 9/2010 | Shimizu et al. |
| 2012/0219901 | A1 | 8/2012 | Bae et al. |

FOREIGN PATENT DOCUMENTS

| | | |
|---|---|---|
| JP | 2008058878 A | 3/2008 |
| JP | 2009080482 A | 4/2009 |
| JP | 2010102061 A | 5/2010 |
| JP | 2010175859 A | 8/2010 |
| JP | 2010197940 A | 9/2010 |
| JP | 2011154214 A | 8/2011 |

OTHER PUBLICATIONS

M. Asano, "Sub-100nm Lithography with KrF Exposure Using Multiple Development Method," Jpn. J. Appl. Phys., vol. 38, 1999, pp. 6999-7003.

V. Truffert et al, "Ultimate contact hole resolution using immersion lithography with line/space imaging," Proc. of SPIE, vol. 7273, 2009, pp. 7274ON-1 thru 7274ON-12.

S. Tarutani, et al, "Development of materials and processes for negative tone development toward 32-nm node 193-nm immersion double-patterning process," Proc. of SPIE, vol. 7273, 2009, pp. 7273OC-1 thru 7273OC-8.

Search Report for corresponding European Application No. 11 16 8171.

PHOTORESIST COMPOSITIONS AND METHODS OF FORMING PHOTOLITHOGRAPHIC PATTERNS

This is a continuation of Application No. 13/149,573, filed May 31, 2011, now U.S. Pat. No. 9,188,864, which claims the benefit of priority of U.S. Provisional Application Ser. No. 61/350,003, filed May 31, 2010.

The invention relates generally to the manufacture of electronic devices. More specifically, this invention relates to photoresist compositions and to photolithographic processes which allow for the formation of fine patterns using a negative tone development process. The photoresist compositions include one or more polymer additive which is substantially non-miscible with a resin component of the resist. Preferred compositions and methods of the invention can result in improvements in defectivity and process window in photolithographic processing.

In the semiconductor manufacturing industry, photoresist materials are used for transferring an image to one or more underlying layers, such as metal, semiconductor and dielectric layers, disposed on a semiconductor substrate, as well as to the substrate itself. To increase the integration density of semiconductor devices and allow for the formation of structures having dimensions in the nanometer (nm) range, photoresists and photolithography processing tools having high-resolution capabilities have been and continue to be developed.

One approach to achieving nm-scale feature sizes in semiconductor devices is the use of short wavelengths of light, for example, 193 nm or less, during exposure of chemically amplified photoresists. Immersion lithography effectively increases the numerical aperture of the lens of the imaging device, for example, a scanner having a KrF or ArF light source. This is accomplished by use of a relatively high refractive index fluid (i.e., an immersion fluid) between the last surface of the imaging device and the upper surface of the semiconductor wafer. The immersion fluid allows a greater amount of light to be focused into the resist layer than would occur with an air or inert gas medium.

The theoretical resolution limit as defined by the Rayleigh equation is shown below:

$$R = k_1 \frac{\lambda}{NA}$$

where $k_1$ is the process factor, $\lambda$ is the wavelength of the imaging tool and NA is the numerical aperture of the imaging lens. When using water as the immersion fluid, the maximum numerical aperture can be increased, for example, from 1.2 to 1.35. For a $k_1$ of 0.25 in the case of printing line and space patterns, 193 nm immersion scanners would only be capable of resolving 36 nm half-pitch line and space patterns. The resolution for printing contact holes or arbitrary 2D patterns is further limited due to the low aerial image contrast with a dark field mask wherein the theoretical limit for $k_1$ is 0.35. The smallest half-pitch of contact holes is thus limited to about 50 nm. The standard immersion lithography process is generally not suitable for manufacture of devices requiring greater resolution.

Considerable effort has been made to extend the practical resolution capabilities of positive tone development in immersion lithography from both materials and processing standpoints. One such example involves negative tone development (NTD) of a traditionally positive-type chemically amplified photoresist. NTD is an image reversal technique allowing for use of the superior imaging quality obtained with bright field masks to print the critical dark field layers. NTD resists typically employ a resin having acid-labile (or acid-cleavable) groups and a photoacid generator. Exposure to actinic radiation causes the photoacid generator to form an acid which, during post-exposure baking, causes cleavage of the acid-labile groups in the resin. As a result, a difference in solubility characteristics in particular organic developers is created between exposed and unexposed regions of the resist such that unexposed regions of the resist are removed by the developer, leaving behind a pattern created by the insoluble exposed regions. Such a process is described, for example, in U.S. Pat. No. 6,790,579, to Goodall et al. That document discloses a photoresist composition comprising an acid-generating initiator and a polycyclic polymer containing recurring acid labile pendant groups along the polymer backbone. The exposed areas can be selectively removed with an alkaline developer or, alternatively, the unexposed regions can be selectively removed by treatment with a suitable nonpolar solvent for negative tone development.

A problem associated with the use of chemically amplified photoresists when printing high resolution patterns in negative tone development processes is surface (or top) inhibition. It is believed that this effect is caused by stray light contacting dark-field regions of the photoresist beneath edges of the mask pattern during exposure. This can give rise to cleavage of the acid-labile groups of the photoresist resin in the dark-field regions immediately adjacent the mask pattern, particularly at the upper surface of the resist. This renders such regions less soluble in the NTD developer than they otherwise would be.

There is a continuing need in the art for improved compositions and photolithographic methods for negative tone development which allow for the formation of fine patterns in electronic device fabrication and which address one or more problems associated with the state of the art.

According to a first aspect of the invention, photoresist compositions are provided. The photoresist compositions comprise: a first polymer which is acid sensitive; a second polymer formed from a monomer having the following general formula (I):

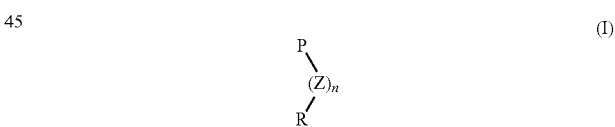

wherein: P is a polymerizable functional group; Z is a spacer unit chosen from optionally substituted linear or branched aliphatic and aromatic hydrocarbons, and combinations thereof, optionally with one or more linking moiety chosen from —O—, —S—, —COO— and —CONR$_1$—, wherein R$_1$ is chosen from hydrogen and substituted and unsubstituted C1 to C10 linear, branched and cyclic hydrocarbons; n is an integer from 0 to 5; and R is chosen from substituted and unsubstituted C1 to C20 linear, branched and cyclic hydrocarbons; wherein the second polymer is acid insensitive and free of fluorine and silicon, and wherein the second polymer has a surface energy lower than a surface energy of the first polymer; a photoacid generator; and a solvent.

According to a further aspect, coated substrates are provided. The coated substrates comprise a substrate and a layer of a photoresist composition of the invention over a surface of the substrate.

According to a further aspect, methods of forming a photolithographic pattern are provided. The methods comprise: (a) providing a substrate comprising one or more layer to be patterned over a surface of the substrate; (b) applying a layer of a photoresist composition of the invention over the one or more layer to be patterned; (c) patternwise exposing the photoresist composition layer to actinic radiation; (d) heating the exposed photoresist composition layer in a post-exposure bake process; and (e) applying a developer to the photoresist composition layer, wherein unexposed portions of the photoresist layer are removed by the developer, leaving a photoresist pattern over the one or more layer to be patterned. The patternwise exposing can be conducted by immersion lithography or, alternatively, using dry exposure techniques.

In accordance with a further aspect, electronic devices formed by the described negative tone development processes are provided.

As used herein: "g" means grams; "L" means liter; "ml" means milliliter; "nm" means nanometer; "Å" means Angstroms; "mol %" means molar percent; "Mw" means weight average molecular weight; "Mn" means number average molecular weight; wt % means weight percent; and the articles "a" and "an" mean one or more.

The present invention will be discussed with reference to the following drawings, in which like reference numerals denote like features, and in which:

FIG. 1A-E illustrates a process flow for forming a photolithographic pattern in accordance with a first exemplary aspect of the invention.

Photoresist Compositions

The photoresist compositions of the invention are particularly suitable for use in negative tone development processes. The photoresist compositions include: a first matrix polymer which is acid-sensitive; a second additive polymer which is acid-insensitive, free of fluorine and silicon, and having a surface energy lower than a surface energy of the first polymer; a photoacid generator; a solvent; and various optional components.

Particularly preferred photoresist compositions of the invention when used in a negative tone development process provide one or preferably more of improved focus latitude and exposure latitude, resist patterns such as lines and contact holes which are uniform in geometry, and reduced defectivity. These benefits can be achieved when using the compositions in dry lithography or immersion lithography processes. When used in immersion lithography, preferred photoresist compositions can further exhibit reduced migration (leaching) of photoresist materials into an immersion fluid. Significantly, this can be achieved without use of a topcoat layer over the photoresist.

The additive polymer migrates toward the upper surface of the resist coating layer during coating of the photoresist composition, thereby forming a surface layer substantially made up of the additive polymer. Following exposure and post exposure bake (PEB), the resist coating layer is developed in a developer, typically an organic solvent. The developer removes unexposed regions of the photoresist layer and the surface layer of the exposed regions. It is believed that removal of the surface layer of the exposed resist portions provides improved resist profiles as a result of the reduction in surface inhibition. Also a result of the additive polymer's surface migration, the photoresist composition layer can, in the case of an immersion lithography process, effectively inhibit migration of photoresist materials out of the resist layer into the immersion fluid.

The photoresist compositions of the invention are preferably chemically-amplified materials. Negative tone development processes generally result in removal of unexposed regions of the resist layer even for what are traditionally referred to as positive-type materials. As used herein, the term positive-type (or positive-working or positive-acting) is used to describe the photoresist compositions in a traditional sense and not based on the final result of the negative tone development process. Typically preferred chemically-amplified positive resist compositions include one or more matrix polymer that includes photoacid-labile groups such as photoacid-labile ester or acetal groups which undergo a photoacid-promoted deprotection reaction on exposure to activating radiation and heat treatment.

A. Matrix Polymer

The photoresist compositions include one or more matrix polymer which is acid-sensitive. This means that the matrix polymer as part of a layer of the photoresist composition undergoes a change in solubility in a developer described herein as a result of reaction with acid generated from the photoacid generator following softbake, exposure to activating radiation and post exposure bake.

For imaging at sub-200 nm wavelengths such as 193 nm, the matrix polymer is typically substantially free (e.g., less than 15 mole %) of phenyl, benzyl or other aromatic groups where such groups are highly absorbing of the radiation. Suitable polymers that are substantially or completely free of aromatic groups are disclosed in European application EP930542A1 and U.S. Pat. Nos. 6,692,888 and 6,680,159, all of the Shipley Company.

In positive-acting chemically amplified photoresist compositions, the matrix polymer typically includes acid labile groups and undergoes a photoacid-promoted deprotection reaction on exposure to activating radiation and heat treatment. Preferable acid labile groups include, for example, acetal groups or ester groups that contain a tertiary non-cyclic alkyl carbon (e.g., t-butyl) or a tertiary alicyclic carbon (e.g., methyladamantyl) covalently linked to a carboxyl oxygen of an ester of the matrix polymer.

Suitable matrix polymers further include polymers that contain alkyl acrylate units, preferably including acid-labile acrylate units, such as t-butyl acrylate, t-butyl methacrylate, methyladamantyl acrylate, methyl adamantyl methacrylate, ethylfenchylacrylate, ethylfenchylmethacrylate, and the like, and other non-cyclic alkyl and alicyclic acrylates. Such polymers have been described, for example, in U.S. Pat. No. 6,057,083, European Published Applications EP01008913A1 and EP00930542A1, and U.S. Pat. No. 6,136,501.

Other suitable matrix polymers include, for example, those which contain polymerized units of a non-aromatic cyclic olefin (endocyclic double bond) such as an optionally substituted norbornene, for example, polymers described in U.S. Pat. Nos. 5,843,624 and 6, 048,664.

Still other suitable matrix polymers include polymers that contain polymerized anhydride units, particularly polymerized maleic anhydride and/or itaconic anhydride units, such as disclosed in European Published Application EP01008913A1 and U.S. Pat. No. 6,048,662.

Also suitable as the matrix polymer is a resin that contains repeat units that contain a hetero atom, particularly oxygen and/or sulfur (but other than an anhydride, i.e., the unit does not contain a keto ring atom). The heteroalicyclic unit can be fused to the polymer backbone, and can comprise a fused carbon alicyclic unit such as provided by polymerization of a norbornene group and/or an anhydride unit such as provided by polymerization of a maleic anhydride or itaconic anhydride. Such polymers are disclosed in PCT/US01/14914 and U.S. Pat. No. 6,306,554. Other suitable heteroatom group containing matrix polymers include polymers that contain polymerized carbocyclic aryl units substituted with one or more hetero-atom (e.g., oxygen or sulfur) containing groups, for example, hydroxy naphthyl groups, such as disclosed in U.S. Pat. No. 7,244,542.

Blends of two or more of the above-described matrix polymers can suitably be used in the photoresist compositions of the invention.

For wavelengths of 200 nm or greater, suitable resin materials include, for example, phenolic resins that contains acid-labile groups that can provide a chemically amplified positive resist particularly suitable for imaging at 248 nm. Particularly preferred resins of this class include: i) polymers that contain polymerized units of a vinyl phenol and an alkyl acrylate, where the polymerized alkyl acrylate units can undergo a deblocking reaction in the presence of photoacid. Exemplary alkyl acrylates that can undergo a photoacid-induced deblocking reaction include e.g. t-butyl acrylate, t-butyl methacrylate, methyladamantyl acrylate, methyl adamantyl methacrylate, and other non-cyclic alkyl and alicyclic acrylates that can undergo a photoacid-induced reaction, such as polymers in U.S. Pat. Nos. 6,042,997 and 5,492,793; ii) polymers that contain polymerized units of a vinyl phenol, an optionally substituted vinyl phenyl (e.g., styrene) that does not contain a hydroxy or carboxy ring substituent, and an alkyl acrylate such as those deblocking groups described with polymers i) above, such as polymers described in U.S. Pat. No. 6,042,997; and iii) polymers that contain repeat units that comprise an acetal or ketal moiety that will react with photoacid, and optionally aromatic repeat units such as phenyl or phenolic groups; such polymers have been described in U.S. Pat. Nos. 5,929,176 and 6,090,526, as well as blends of i) and/or ii) and/or iii). Also suitable are phenolic resins that do not contain acid-labile groups such as poly(vinylphenol) and novolak resins that may be employed in I-line and G-line photoresists together with a diazonaphthoquinone photoactive compound and have been described e.g. in U.S. Pat. Nos. 4,983,492; 5,130,410; 5,216,111; and 5,529,880.

Suitable matrix polymers for use in the photoresist compositions of the invention are commercially available and can readily be made by persons skilled in the art. The matrix polymer is present in the resist composition in an amount sufficient to render an exposed coating layer of the resist developable in a suitable developer solution. Typically, the matrix polymer is present in the composition in an amount of from 50 to 95 wt % based on total solids of the resist composition. The weight average molecular weight $M_w$ of the matrix polymer is typically less than 100,000, for example, from 5000 to 100,000, more typically from 5000 to 15,000.

B. Additive Polymer

The additive polymer is a material that has a lower surface energy than that of the matrix polymer and should be substantially non-miscible with the matrix polymer. In this way, segregation or migration of the first additive to the top or upper portions of an applied photoresist layer during the coating process is facilitated.

Further, the additive polymer is acid-insensitive. This means that the additive polymer as part of a layer of the photoresist composition does not react with acid generated from the photoacid generator following softbake, exposure to activating radiation and post exposure bake. The additive polymer should therefore be free of photoacid-labile groups, such as photoacid-labile ester or acetal groups, which groups are typically included in matrix polymers of positive-acting chemically amplified photoresists. As a result of the additive polymer's migration to the resist surface during coating and its acid-inactivity, micro-bridge defects in trench formation and missing contact hole defects caused by the presence of stray light in regions of the resist blocked by a photomask can be minimized or avoided.

The additive polymer is further free of silicon and fluorine. Silicon-containing polymers exhibit a significantly lower etch rate than organic photoresist polymers in certain etchants. As a result, aggregation of a silicon-containing additive polymer at the surface of an organic matrix polymer-based resist layer can cause cone defects during the etching process. It is therefore desired that the additive polymer not contain silicon. Avoidance of fluorine-containing additive polymers is similarly desired. In this regard, the hydrophobic nature of certain fluorine-based polymers can be problematic as a result of their limited solubility in organic solvents useful in negative tone development. As well, it is desired to reduce the use of fluorinated materials for environmental purposes.

Preferred additive polymers are soluble in the same organic solvent(s) used to formulate the photoresist composition. Preferred additive polymers also will be soluble or become soluble upon post exposure bake (e.g., 120° C. for 60 seconds) in organic developers used in negative tone development processes.

The additive polymer can be linear, branched or hyperbranched. As referred to herein, "hyperbranched polymers" include those materials known as "hyperbranched polymers" under the IUPAC nomenclature. See IUPAC. Compendium of Macromolecular Nomenclature (The Purple Book); Metanomski, W. V., Ed.; Blackwell Scientific Publications, Oxford, UK, 1991. Thus, by this nomenclature, a hyperbranched polymer has structural repeating units (or constitutional repeating unit as referred to by IUPAC) where such structural repeating units each has a covalent connectivity of more than two. Particularly preferred hyperbranched polymers may have minimal (e.g., less than 5, 4, 3, 2 or 1 weight percent) aromatic content, or be completely free of any aromatic content. Hyperbranched polymers that have one or more acrylate repeat units may be particularly suitably for many applications. Also preferred are additive polymers that are formed from multi-functional acrylate monomers, for example, acrylate monomers that have multiple vinyl groups such as trimethypropane triacrylate (TMPTA).

The second polymer is formed from a monomer having the following general formula (I):

wherein: P is a polymerizable functional group; Z is a spacer unit chosen from optionally substituted linear or branched aliphatic and aromatic hydrocarbons, and combinations thereof, optionally with one or more linking moiety chosen from —O—, —S—, —COO—, —CONR$_1$—, wherein R$_1$ is chosen from hydrogen and substituted and unsubstituted C1 to C10 linear, branched and cyclic hydrocarbons, preferably alkyl; n is an integer from 0 to 5; and R is chosen from substituted and unsubstituted C1 to C20, typically C1 to C6, linear, branched and cyclic hydrocarbons, preferably alkyl.

R can, for example, be represented by the formula $C_nH_{2n+1}$, wherein n is an integer from 1 to 20, typically from 1 to 6.

The polymerizable functional group P can be chosen, for example, from the following general formulae (I-A), (I-B) and (I-C):

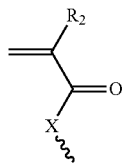
(I-A)

wherein $R_2$ is chosen from hydrogen and substituted and unsubstituted C1 to C3 alkyl; and X is oxygen or is represented by the formula $NR_3$, wherein $R_3$ is chosen from hydrogen and substituted and unsubstituted C1 to C10 linear, branched and cyclic hydrocarbons;

(I-B)

wherein $R_4$ is chosen from hydrogen and substituted and unsubstituted C1 to C3 alkyl; and

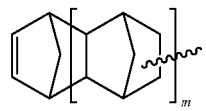
(I-C)

wherein m is an integer from 0 to 3.

Suitable additive polymers and monomers for making the additive polymers for use in the photoresist compositions of the invention are commercially available and/or can be made by persons skilled in the art. Exemplary suitable monomers of general formula (I) are described below, but are not limited to these structures. For purposes of these structures, "$R_2$" and "X" are as defined above.

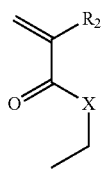
(I-1)

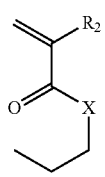
(I-2)

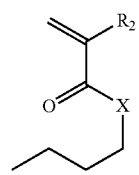
(I-3)

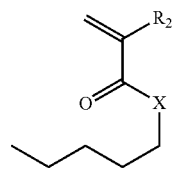
(I-4)

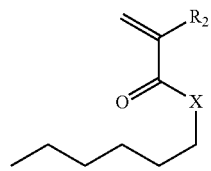
(I-5)

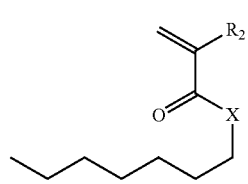
(I-6)

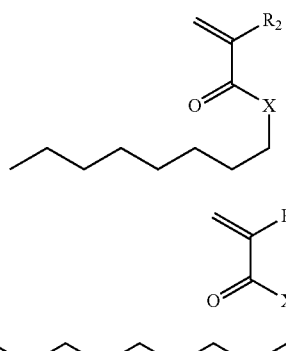
(I-7)

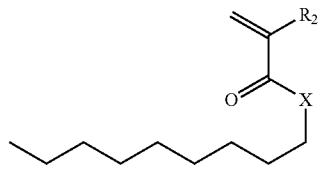
(I-8)

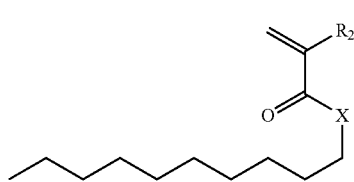
(I-9)

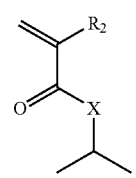
(I-10)

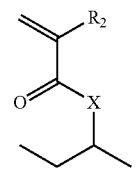
(I-11)

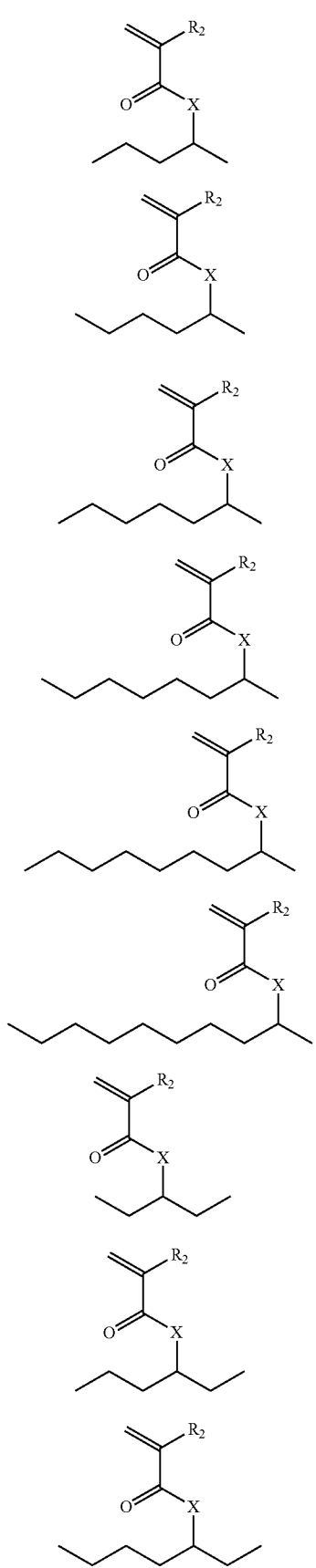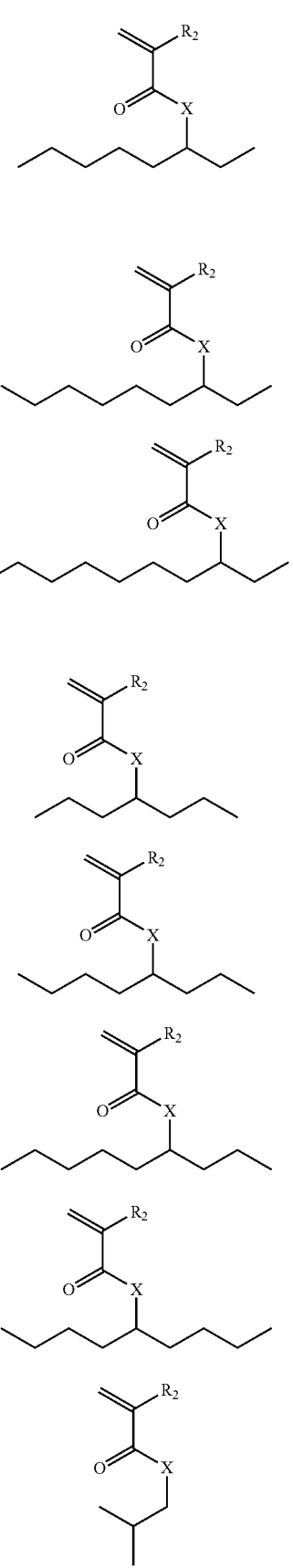

-continued
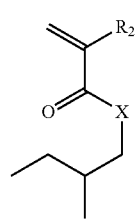 (I-29)
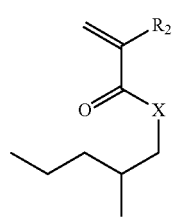 (I-30)
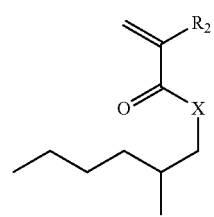 (I-31)
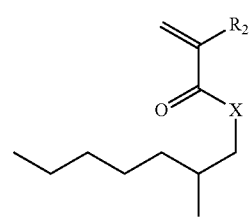 (I-32)
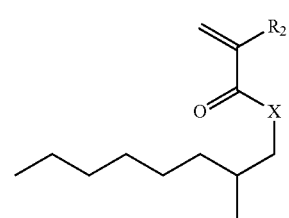 (I-33)
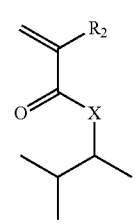 (I-34)
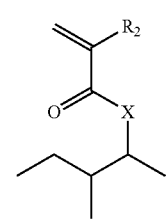 (I-35)
-continued
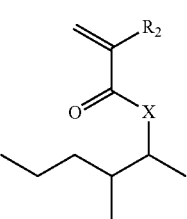 (I-36)
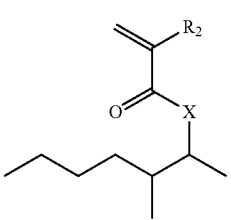 (I-37)
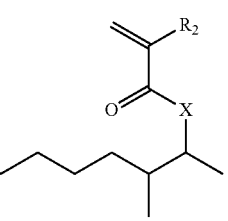 (I-38)
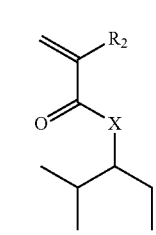 (I-39)
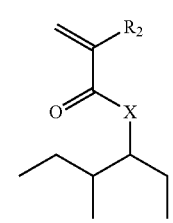 (I-40)
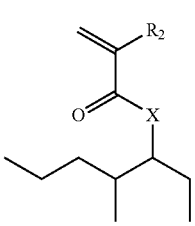 (I-41)
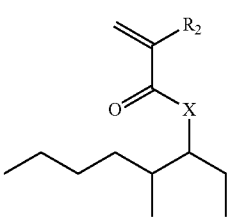 (I-42)

-continued
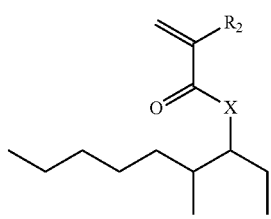
(I-43)
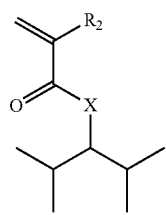
(I-44)
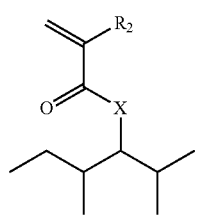
(I-45)
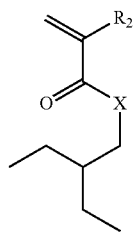
(I-46)
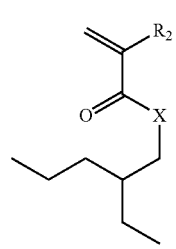
(I-47)
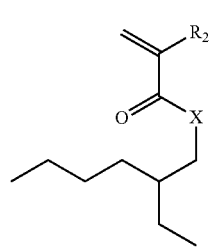
(I-48)
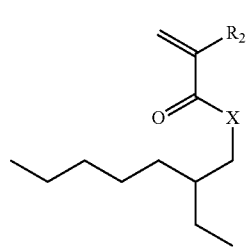
(I-49)
-continued
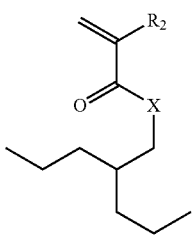
(I-50)
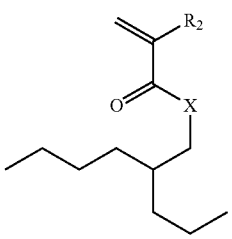
(I-51)
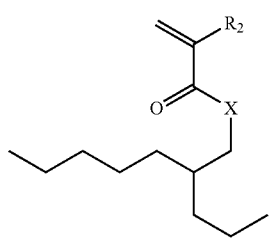
(I-52)
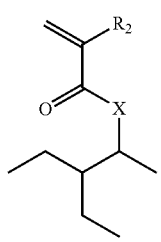
(I-53)
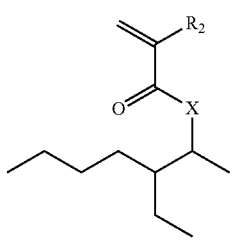
(I-54)
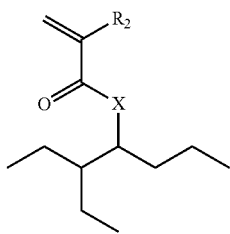
(I-55)

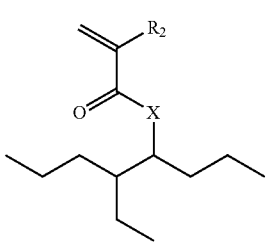 (I-56)
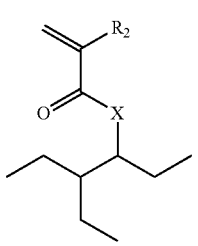 (I-57)
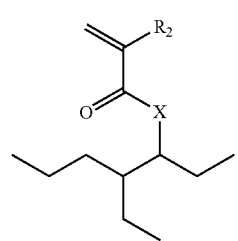 (I-58)
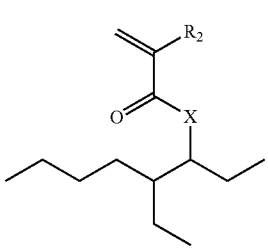 (I-59)
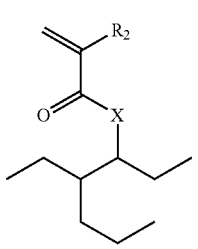 (I-60)
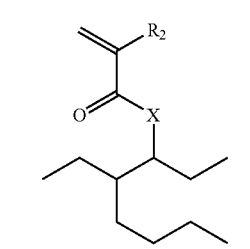 (I-61)
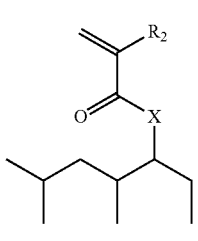 (I-62)
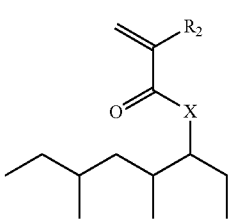 (I-63)
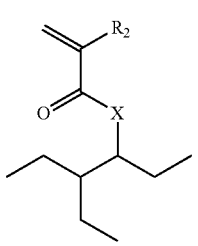 (I-64)
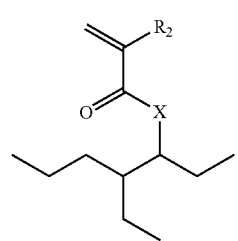 (I-65)
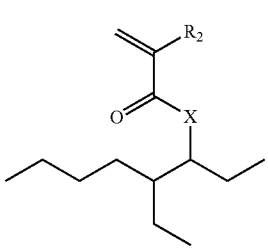 (I-66)
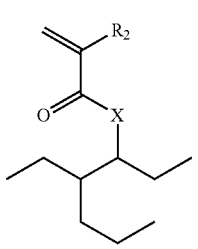 (I-67)
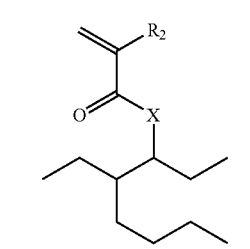 (I-68)
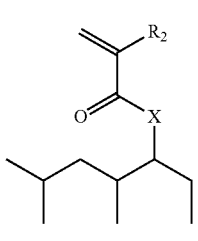 (I-69)

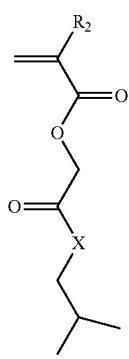 (I-70)
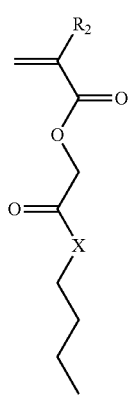 (I-71)
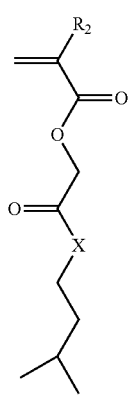 (I-72)
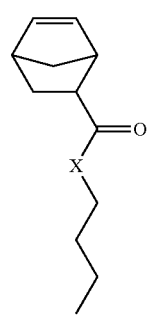 (I-73)
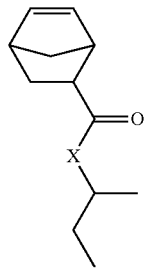 (I-74)
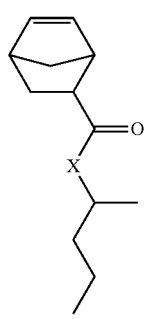 (I-75)
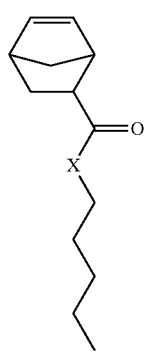 (I-76)
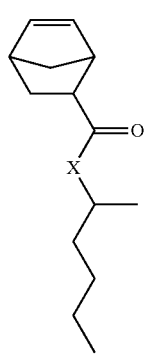 (I-77)
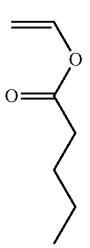 (I-78)

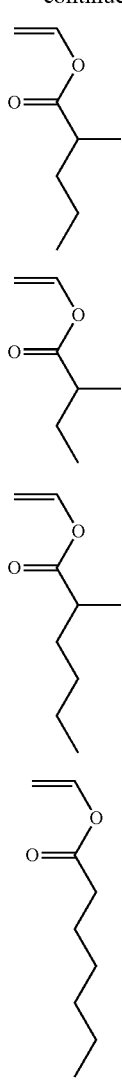

(I-79)

(I-80)

(I-81)

(I-82)

Of these structures, the monomers of structures I-2 to I-4 and I-78 to I-82 are preferred.

The one or more additive polymer typically may be present in the photoresist composition in relatively small amounts and still provide effective results. The content of the additive polymer may depend, for example, on whether the lithography is a dry or immersion-type process. For example, the additive polymer lower limit for immersion lithography is generally dictated by the need to prevent leaching of the resist components. A higher additive polymer content will typically result in pattern degradation. The one or more polymer additive is typically present in the compositions of the invention in an amount of from 0.1 to 10 wt %, more typically from 1 to 5 wt %, based on total solids of the photoresist composition. The weight average molecular weight of the additive polymer is typically less than 400,000, for example from 5000 to 50,000.

C. Photoacid Generator

The photosensitive composition further comprises a photoacid generator (PAG) employed in an amount sufficient to generate a latent image in a coating layer of the composition upon exposure to activating radiation. For example, the photoacid generator will suitably be present in an amount of from about 1 to 20 wt % based on total solids of the photoresist composition. Typically, lesser amounts of the photoactive component will be suitable for chemically amplified resists.

Suitable PAGs are known in the art of chemically amplified photoresists and include, for example: onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate;, nitrobenzyl derivatives, for example, 2-nitrobenzyl p-toluenesulfonate, 2,6-dinitrobenzyl p-toluenesulfonate, and 2,4-dinitrobenzyl p-toluenesulfonate; sulfonic acid esters, for example, 1,2,3-tris(methanesulfonyloxy)benzene, 1,2,3-tris (trifluoromethanesulfonyloxy)benzene, and 1,2,3-tris(p-toluenesulfonyloxy)benzene; diazomethane derivatives, for example, bis(benzenesulfonyl)diazomethane, bis(p-toluenesulfonyl)diazomethane; glyoxime derivatives, for example, bis-O-(p-toluenensulfonyl)-α-dimethylglyoxime, and bis-O-(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4,6-bis(trichloromethyl)-1, 3,5-triazine, and 2-(4-methoxynaphthyl)-4,6-bis(trichloromethyl)-1,3,5-triazine. One or more of such PAGs can be used.

D. Solvent

Suitable solvents for the photoresist compositions of the invention include, for example: glycol ethers such as 2-methoxyethyl ether (diglyme), ethylene glycol monomethyl ether, and propylene glycol monomethyl ether; propylene glycol monomethyl ether acetate; lactates such as methyl lactate and ethyl lactate; propionates such as methyl propionate, ethyl propionate, ethyl ethoxy propionate and methyl-2-hydroxy isobutyrate; Cellosolve esters such as methyl Cellosolve acetate; aromatic hydrocarbons such as toluene and xylene; and ketones such as methylethyl ketone, cyclohexanone and 2-heptanone. A blend of solvents such as a blend of two, three or more of the solvents described above also are suitable. The solvent is typically present in the composition in an amount of from 90 to 99 wt %, more typically from 95 to 98 wt %, based on the total weight of the photoresist composition.

E. Optional Components

The photoresist compositions can also include other optional materials. For example, negative-acting resist compositions typically also include a crosslinker component. Suitable crosslinker components include, for example, an amine-based material such as a melamine resin, that will cure, crosslink or harden upon exposure to acid on exposure of a photoacid generator to activating radiation. Preferred crosslinkers include amine-based materials, including melamine, glycolurils, benzoguanamine-based materials and urea-based materials. Melamine-formaldehyde resins are generally most preferred. Such crosslinkers are commercially available, e.g. the melamine resins sold by American Cyanamid under the trade names Cymel 300, 301 and 303. Glycoluril resins are sold by American Cyanamid under trade names Cymel 1170, 1171, 1172, urea-based resins are sold under the trade names of Beetle 60, 65 and 80, and benzoguanamine resins are sold under the trade names Cymel 1123 and 1125. For imaging at sub-200 nm wavelengths such as 193 nm, preferred negative-acting photoresists are disclosed in WO 03077029 to the Shipley Company.

Other optional additives for positive- or negative-acting compositions include, for example, actinic and contrast dyes, anti-striation agents, plasticizers, speed enhancers, sensitizers, and the like. Such optional additives if used are typically present in the composition in minor amounts such as from 0.1 to 10 wt % based on total solids of the photoresist composition, although fillers and dyes can be present in relatively large concentrations, for example, from 5 to 30 wt % based on total solids of the photoresist composition.

A preferred optional additive of resist compositions of the invention is an added base, for example, a caprolactam, which can enhance resolution of a developed resist relief image. The added base is suitably used in relatively small amounts, for example, from 1 to 20 wt % relative to the PAG, more typically from 5 to 15 wt % relative to the PAG. Other suitable basic additives include: alkyl amines such as tripropylamine and dodecylamine, aryl amines such as diphenylamine, triphenylamine, aminophenol, 2-(4-aminophenyl)-2-(4-hydroxyphenyl)propane, and the like.

Preparation of Photoresist Compositions

The photoresists used in accordance with the invention are generally prepared following known procedures. For example, a resist of the invention can be prepared as a coating composition by dissolving the components of the photoresist in a suitable solvent, for example, one or more of: a glycol ether such as 2-methoxyethyl ether (diglyme), ethylene glycol monomethyl ether, propylene glycol monomethyl ether; propylene glycol monomethyl ether acetate; lactates such as ethyl lactate or methyl lactate, with ethyl lactate being preferred; propionates, particularly methyl propionate, ethyl propionate and ethyl ethoxy propionate; a Cellosolve ester such as methyl Cellosolve acetate; an aromatic hydrocarbon such toluene or xylene; or a ketone such as methylethyl ketone, cyclohexanone and 2-heptanone. The desired total solids content of the photoresist will depend on factors such as the particular polymers in the composition, final layer thickness and exposure wavelength. Typically the solids content of the photoresist varies from 1 to 10 wt %, more typically from 2 to 5 wt %, based on the total weight of the photoresist composition.

Negative Tone Development Methods

The invention further provides methods for forming a photoresist relief image and producing an electronic device using photoresists of the invention. The invention also provides novel articles of manufacture comprising substrates coated with a photoresist composition of the invention. Processes in accordance with the invention will now be described with reference to FIG. 1A-E, which illustrates a first exemplary process flow for forming a photolithographic pattern by negative tone development.

FIG. 1A depicts in cross-section a substrate 100 which may include various layers and features. The substrate can be of a material such as a semiconductor, such as silicon or a compound semiconductor (e.g., III-V or II-VI), glass, quartz, ceramic, copper and the like. Typically, the substrate is a semiconductor wafer, such as single crystal silicon or compound semiconductor wafer, and may have one or more layers and patterned features formed on a surface thereof. One or more layers to be patterned 102 may be provided over the substrate 100. Optionally, the underlying base substrate material itself may be patterned, for example, when it is desired to form trenches in the substrate material. In the case of patterning the base substrate material itself, the pattern shall be considered to be formed in a layer of the substrate.

The layers may include, for example, one or more conductive layers such as layers of aluminum, copper, molybdenum, tantalum, titanium, tungsten, alloys, nitrides or silicides of such metals, doped amorphous silicon or doped polysilicon, one or more dielectric layers such as layers of silicon oxide, silicon nitride, silicon oxynitride, or metal oxides, semiconductor layers, such as single-crystal silicon, and combinations thereof. The layers to be etched can be formed by various techniques, for example, chemical vapor deposition (CVD) such as plasma-enhanced CVD, low-pressure CVD or epitaxial growth, physical vapor deposition (PVD) such as sputtering or evaporation, or electroplating. The particular thickness of the one or more layers to be etched 102 will vary depending on the materials and particular devices being formed.

Depending on the particular layers to be etched, film thicknesses and photolithographic materials and process to be used, it may be desired to dispose over the layers 102 a hard mask layer 104 and/or a bottom antireflective coating (BARC) 106 over which a photoresist layer 108 is to be coated. Use of a hard mask layer 104 may be desired, for example, with very thin resist layers, where the layers to be etched require a significant etching depth, and/or where the particular etchant has poor resist selectivity. Where a hard mask layer is used, the resist patterns to be formed can be transferred to the hard mask layer which, in turn, can be used as a mask for etching the underlying layers 102. Suitable hard mask materials and formation methods are known in the art. Typical materials include, for example, tungsten, titanium, titanium nitride, titanium oxide, zirconium oxide, aluminum oxide, aluminum oxynitride, hafnium oxide, amorphous carbon, silicon oxynitride and silicon nitride. The hard mask layer 104 can include a single layer or a plurality of layers of different materials. The hard mask layer can be formed, for example, by chemical or physical vapor deposition techniques.

A bottom antireflective coating 106 may be desirable where the substrate and/or underlying layers would otherwise reflect a significant amount of incident radiation during photoresist exposure such that the quality of the formed pattern would be adversely affected. Such coatings can improve depth-of-focus, exposure latitude, linewidth uniformity and CD control. Antireflective coatings are typically used where the resist is exposed to deep ultraviolet light (300 nm or less), for example, KrF excimer laser light (248 nm) or ArF excimer laser light (193 nm). The antireflective coating 106 can comprise a single layer or a plurality of different layers. Suitable antireflective materials and methods of formation are known in the art. Antireflective materials are commercially available, for example, those sold under the AR™ trademark by Rohm and Haas Electronic Materials LLC (Marlborough, Mass. USA), such as AR™40A and AR™124 antireflectant materials.

A photoresist composition as described herein is applied on the substrate over the antireflective layer 106 (if present) to form a photoresist layer 108. The photoresist composition can be applied to the substrate by spin-coating, dipping, roller-coating or other conventional coating technique. Of these, spin-coating is typical. For spin-coating, the solids content of the coating solution can be adjusted to provide a desired film thickness based upon the specific coating equipment utilized, the viscosity of the solution, the speed of the coating tool and the amount of time allowed for spinning A typical thickness for the photoresist layer 108 is from about 500 to 3000 Å.

The photoresist layer can next be softbaked to minimize the solvent content in the layer, thereby forming a tack-free coating and improving adhesion of the layer to the substrate. The softbake can be conducted on a hotplate or in an oven, with a hotplate being typical. The softbake temperature and time will depend, for example, on the particular material of the photoresist and thickness. Typical softbakes are conducted at a temperature of from about 90 to 150° C., and a time of from about 30 to 90 seconds.

The methods of the invention can be used with a variety of imaging wavelengths, for example, radiation having a wavelength of sub-400 nm, sub-300 or sub-200 nm exposure wavelength, with 248 nm and 193 nm being typical exposure wavelengths. In an exemplary aspect, the photoresists are suitable for use with and imaged at a sub-200 nm wavelength such as 193 nm. At such wavelengths, the methods find use in immersion or dry (non-immersion) lithography techniques. For immersion lithography, use of a topcoat layer is unnecessary as the photoresist composition can perform functions performed by a topcoat layer, for example, prevention of photoresist component leaching into the immersion fluid, which otherwise can result in contamination of the optical lens and change in the effective refractive index and transmission properties of the immersion fluid. As described above, this effect is believed to be due to migration of the additive polymer to the upper surface of the resist coating layer to form a surface layer substantially made up of the additive polymer.

The photoresist layer 108 is next exposed to activating radiation 110 through a first photomask 112 to create a difference in solubility between exposed and unexposed regions. References herein to exposing a photoresist composition to radiation that is activating for the composition indicates that the radiation is capable of forming a latent image in the photoresist composition. The photomask has optically transparent and optically opaque regions 113, 114 correspond to regions of the resist layer to remain and be removed, respectively, in a subsequent development step for a positive-acting material as illustrated. Typical imaging wavelengths of lithographic systems of the invention include those described above, with sub-200 nm wavelengths such as 193 nm being preferable. The exposure energy is typically from about 20 to 80 mJ/cm$^2$, dependent upon the exposure tool and the components of the photosensitive composition.

Figure 1B:
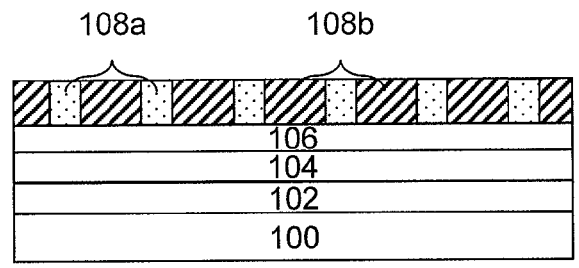

As shown in FIG. 1B, the exposed resist layer is made up of unexposed and exposed regions 108a, 108b. Following exposure of the photoresist layer 108, a post-exposure bake (PEB) is performed. The PEB can be conducted, for example, on a hotplate or in an oven. Conditions for the PEB will depend, for example, on the particular material of the photoresist layer and thickness. The PEB is typically conducted at a temperature of from about 80 to 150° C., and a time of from about 30 to 90 seconds.

Figure 1C:
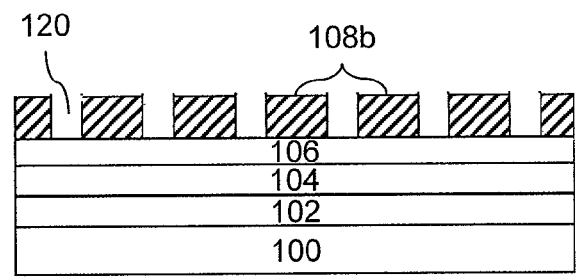

The exposed photoresist layer is next developed to remove unexposed regions 108a, leaving exposed regions 108b forming a resist pattern as shown in FIG. 1C. The developer is typically an organic developer, for example, a solvent chosen from ketones, esters, ethers, hydrocarbons, and mixtures thereof. Suitable ketone solvents include, for example, acetone, 2-hexanone, 5-methyl-2-hexanone, 2-heptanone, 4-heptanone, 1-octanone, 2-octanone, 1-nonanone, 2-nonanone, diisobutyl ketone, cyclohexanone, methylcyclohexanone, phenylacetone, methyl ethyl ketone and methyl isobutyl ketone. Suitable ester solvents include, for example, methyl acetate, butyl acetate, ethyl acetate, isopropyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate and propyl lactate. Suitable ether solvents include, for example, dioxane, tetrahydrofuran and glycol ether solvents, for example, ethylene glycol monomethyl ether, propylene glycol monomethyl ether, ethylene glycol monoethyl ether, propylene glycol monoethyl ether, diethylene glycol monoethyl ether, triethylene glycol monoethyl ether and methoxymethyl butanol. Suitable amide solvents include, for example, N-methyl-2-pyrrolidone, N,N-dimethylacetamide and N,N-dimethylformamide. Suitable hydrocarbon solvents include, for example, aromatic hydrocarbon solvents such as toluene and xylene. In addition, mixtures of these solvents, or one or more of the listed solvents mixed with a solvent other than those described above or mixed with water can be used. Of these, 2-heptanone and 5-methyl-2-hexanone are particularly preferred. Other suitable solvents include those used in the photoresist composition.

The solvent can be present as a substantially pure material, for example, in an amount greater than 95 wt %, greater than 98 wt % or greater than 99 wt %, based on the total weight of the developer. In the case a mixture of solvents are used in the developer, the boiling points of the solvents are preferably similar. The solvents of the developer are typically present in an amount of from 50 wt % to 100 wt %, more typically from 80 wt % to 100 wt %, based on the total weight of the developer.

The developer material may include optional additives, for example, surfactants such as described above with respect to the photoresist. Such optional additives typically will be present in minor concentrations, for example, in amounts of from about 0.01 to 5 wt % based on the total weight of the developer.

The developer can be applied to the substrate by known techniques, for example, by spin-coating or puddle-coating. The development time is for a period effective to remove the unexposed regions of the photoresist, with a time of from 5 to 30 seconds being typical, and is typically conducted at room temperature.

Preferably, the development process can be conducted without use of a cleaning rinse following development. In this regard, it has been found that the development process can result in a residue-free wafer surface rendering such extra rinse step unnecessary.

Figure 1D:
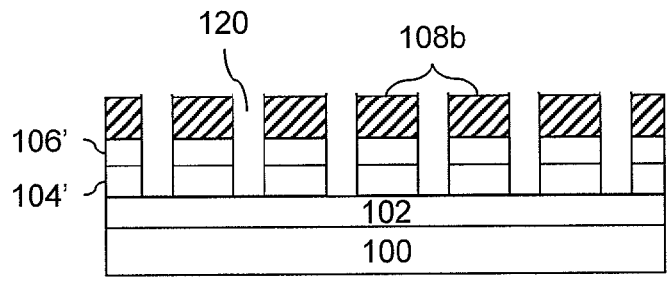

The BARC layer 106, if present, is selectively etched using resist pattern 108b as an etch mask, exposing the underlying hardmask layer 104, as shown in FIG. 1D. The hardmask layer is next selectively etched, again using the resist pattern 108b as an etch mask, resulting in patterned BARC and hardmask layers 106', 104'. Suitable etching techniques and chemistries for etching the BARC layer and hardmask layer are known in the art and will depend, for example, on the particular materials of these layers. Dry-etching processes such as reactive ion etching are typical. The resist pattern 108b and patterned BARC layer 106' are next removed from the substrate using known techniques, for example, oxygen plasma ashing.

Figure 1E:
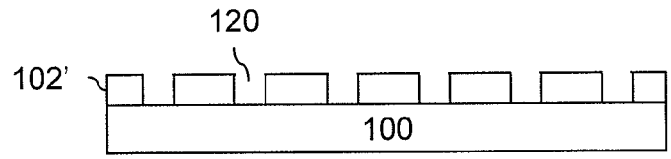

Using the hardmask pattern 104' as an etch mask, the one or more layers 102 are selectively etched. Suitable etching techniques and chemistries for etching the underlying layers 102 are known in the art, with dry-etching processes such as reactive ion etching being typical. The patterned hardmask layer 104' can next be removed from the substrate surface using known techniques, for example, a dry-etching process such as reactive ion etching. The resulting structure is a pattern of etched features 102' as illustrated in FIG. 1E. In an alternative exemplary method, it may be desirable to pattern the layer 102 directly using the resist pattern 108b without the use of a hardmask layer 104. Whether direct patterning is employed will depend on factors such as the materials involved, resist selectivity, resist pattern thickness and pattern dimensions.

The negative tone development methods of the invention are not limited to the exemplary methods described above. For example, the photoresist compositions of the invention can be used in a negative tone development double exposure method for making contact holes. An exemplary such process is a variation of the technique described with reference to FIG. 1, but using an additional exposure of the photoresist layer in a different pattern than the first exposure. In this process, the photoresist layer is exposed to actinic radiation through a photomask in a first exposure step. The photomask includes a series of parallel lines forming the opaque regions of the mask. Following the first exposure, a second exposure of the photoresist layer is conducted through a second photomask that includes a series of lines in a direction perpendicular to those of the first photomask. This pattern can be made simply by rotating the first photomask 90°. The resulting photoresist layer includes unexposed regions, once-exposed regions and twice-exposed regions.

Following the second exposure, the photoresist layer is post-exposure baked and developed using a developer as described above. Unexposed regions corresponding to points of intersection of the lines of the two masks are removed, leaving behind the once- and twice-exposed regions of the resist. The resulting structure can next be patterned as described above with reference to FIG. 1. This method is particularly suited to formation of contact holes in the manufacture of electronic devices.

EXAMPLES

Matrix Polymer Synthesis

The following monomers were employed in the syntheses of matrix polymers in the examples below:

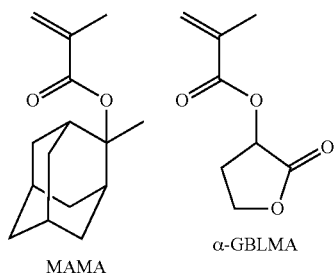

MAMA α-GBLMA

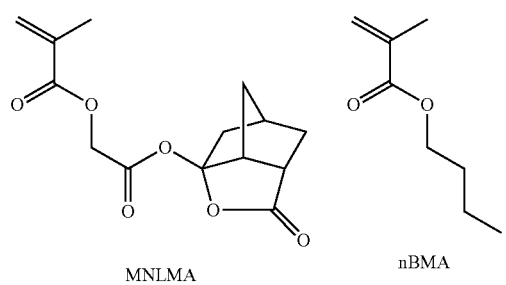

MNLMA nBMA

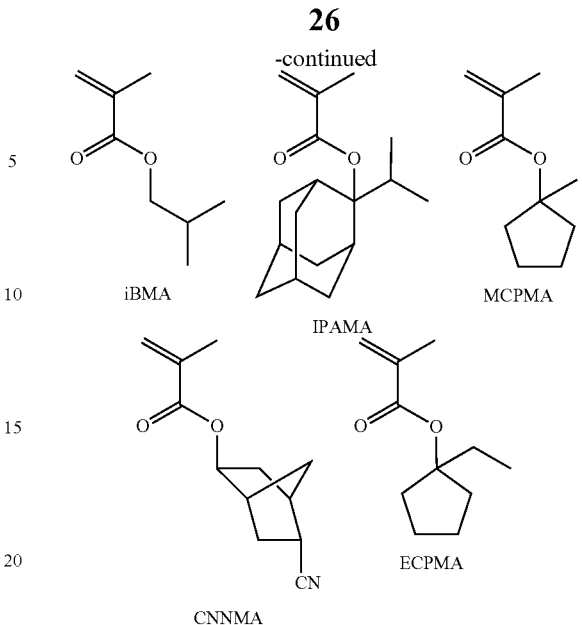

iBMA IPAMA MCPMA

CNNMA ECPMA

Example 1

MAMA/α-GBLMA/MNLMA Matrix Polymer Synthesis 27.48 g MAMA, 15.96 g α-GBLMA, and 6.57 g MNLMA were dissolved in 62 g of PGMEA. The mixture was degassed by bubbling with nitrogen for 20 minutes. A 500 mL flask equipped with a condenser, nitrogen inlet and mechanical stirrer was charged with 35 g PGMEA and the solution was brought to a temperature of 80° C. 2.52 g of V-601 azo initiator (dimethyl-2,2'-azobis(2-methylpropionate) (Wako Specialty Chemicals) dissolved in 2.0 g of PGMEA was charged into the flask. The monomer solution was fed into the reactor at a rate of 27.42 mL/h. After one hour, 1.26 g of V-601 azo initiator dissolved in 2.0 g of PGMEA was added to the reactor and the monomer feeding was carried out for another three hours. After monomer feeding was complete, the polymerization mixture was stirred for an additional three hours at 80° C. After seven hours polymerization (four hours feeding and 3 hours stirring), the polymerization mixture was cooled to room temperature. Precipitation was carried out in 2.0 L of isopropyl alcohol. After filtration, the polymer was dried, re-dissolved in 162 g of THF, re-precipitated into 3.2 L of isopropyl alcohol, filtered, and dried in a vacuum oven at 45° C. for 48 hours to give 41.5 g of the following Matrix Polymer A (Mw=6,498 and Mw/Mn=1.62):

Matrix Polymer A

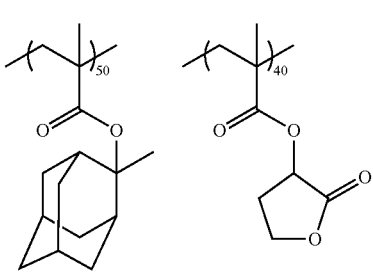

-continued

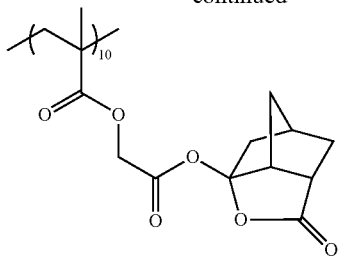

Example 2

IPAMA/MAMA/α-GBLMA/MNLMA Matrix Polymer Synthesis 14.47 g IPAMA, 18.09 g MAMA, 11.26 g α-GBLMA, and 6.18 g MNLMA were dissolved in 62 g of PGMEA. The mixture was degassed by bubbling with nitrogen for 20 minutes. A 500 mL flask equipped with a condenser, nitrogen inlet and mechanical stirrer was charged with 35 g of PGMEA and the solution was brought to a temperature of 80° C. 2.03 g of V-601 azo initiator dissolved in 2.0 g of PGMEA was charged into the flask. The monomer solution was fed into the reactor at a rate of 27.42 mL/h. After one hour, 1.01 g of V-601 azo initiator dissolved in 2.0 g of PGMEA was added to the reactor and the monomer feeding was carried out for another three hours. After monomer feeding was complete, the polymerization mixture was stirred for an additional three hours at 80° C. After seven hours polymerization (four hours feeding and three hours stirring), the polymerization mixture was cooled to room temperature. Precipitation was carried out in 2.0 L of isopropyl alcohol. After filtration, the polymer was dried, re-dissolved in 134 g of THF, re-precipitated into 2.7 L of isopropyl alcohol, filtered, and dried in a vacuum oven at 45° C. for 48 hours to give 36.0 g of the following Matrix Polymer B (Mw=7,814 and Mw/Mn=1.65):

Matrix Polymer B

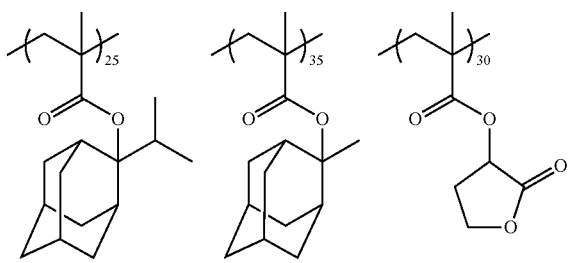

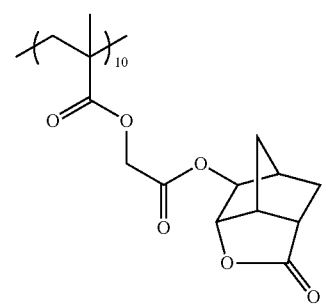

Example 3

IPAMA/MCPMA/α-GBLMA/MNLMA Matrix Polymer Synthesis 51.56 g IPAMA, 46.28 g MCPMA, 40.13 g α-GBLMA, and 22.03 g MNLMA were dissolved in 88 g of THF. The mixture was degassed by bubbling with nitrogen for 20 minutes. A 500 mL flask equipped with a condenser, nitrogen inlet and mechanical stirrer was charged with 56 g of THF and the solution was brought to a temperature of 67° C. 25.34 g of V-601 azo initiator dissolved in 25 g of THF was charged into the flask. The monomer solution was fed into the reactor at a rate of 68.79 mL/h. The monomer feeding was carried out for three hours 30 minutes. After monomer feeding was complete, the polymerization mixture was stirred for an additional 30 minutes at 67° C. After four hours polymerization (three hours 30 minutes feeding and 30 minutes stirring), 80 g of THF was added and the polymerization mixture was cooled down to room temperature. Precipitation was carried out in 5.0 L of isopropyl alcohol. After filtration, the polymer was dried, re-dissolved in 417 g of THF, re-precipitated into 8.3 L of isopropyl alcohol, filtered, and dried in a vacuum oven at 45° C. for 48 hours to give 113.3 g of the following Matrix Polymer C (Mw=8,895 and Mw/Mn=1.67):

Matrix Polymer C

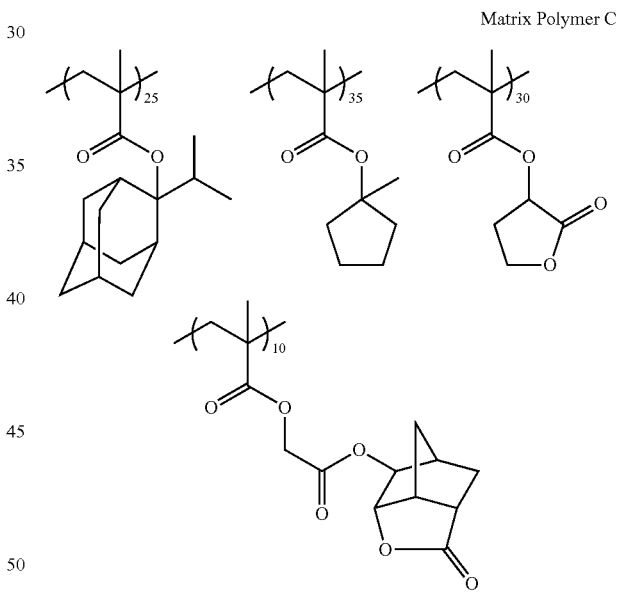

Example 4

MAMA/α-GBLMA/CNNMA Matrix Polymer Synthesis 25.46 g MAMA, 13.15 g α-GBLMA, and 11.40 g CNNMA were dissolved in 62 g of PGMEA. The mixture was degassed by bubbling with nitrogen for 20 minutes. A 500 mL flask equipped with a condenser, nitrogen inlet and mechanical stirrer was charged with 35 g of PGMEA and the solution was brought to a temperature of 80° C. 1.33 g of V-601 azo initiator dissolved in 2.0 g of PGMEA was charged into the flask. The monomer solution was fed into the reactor at a rate of 27.42 mL/h. After one hour, 0.67 g of V-601 azo initiator dissolved in 2.0 g of PGMEA was added to the reactor and the monomer feeding was carried out for another three hours. After monomer feeding was complete, the polymerization mixture was stirred for an additional three hours at 80° C. After a total of seven hours polymerization (four hours feeding and three hours stirring), the polymerization mixture was cooled to room temperature. Precipitation was carried out in 2.0 L of isopropyl alcohol. After filtration, the polymer was dried, re-dissolved in 124 g of THF, re-precipitated into 2.6 L of isopropyl alcohol, filtered, and dried in a vacuum oven at 45° C. for 48 hours to give 42.3 g of the following Matrix Polymer D (Mw=17,814 and Mw/Mn=1.66):

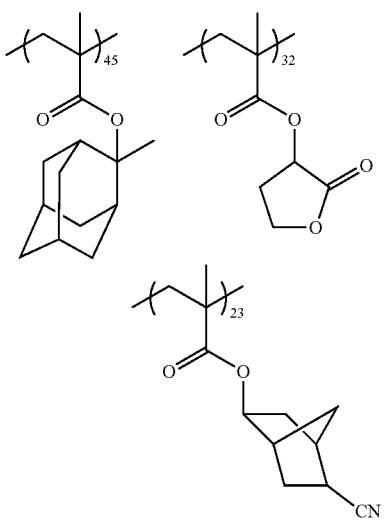

Matrix Polymer D

Example 5

ECPMA/α-GBLMA/CNNMA Matrix Polymer Synthesis 22.33 g ECPMA, 14.82 g α-GBLMA, and 12.85 g CNNMA were dissolved in 62 g of PGMEA. The mixture was degassed by bubbling with nitrogen for 20 minutes. A 500 mL flask equipped with a condenser, nitrogen inlet and mechanical stirrer was charged with 35 g of PGMEA and the solution was brought to a temperature of 80° C. 2.51 g of V-601 azo initiator dissolved in 2.0 g of PGMEA was charged into the flask. The monomer solution was fed into the reactor at a rate of 27.42 mL/h. After one hour, 1.25 g of V-601 azo initiator dissolved in 2.0 g of PGMEA was added to the reactor and the monomer feeding was carried out for another three hours. After monomer feeding was complete, the polymerization mixture was stirred for an additional three hours at 80° C. After a total of 7 hours polymerization (four hours feeding and three hours stirring), the polymerization mixture was cooled to room temperature. Precipitation was carried out in 2.0 L of isopropyl alcohol. After filtration, the polymer was dried, re-dissolved in 135 g of THF, re-precipitated into 2.7 L of isopropyl alcohol, filtered, and dried in a vacuum oven at 45° C. for 48 hours to give 43.6 g of the following Matrix Polymer E (Mw=8,654 and Mw/Mn=1.63):

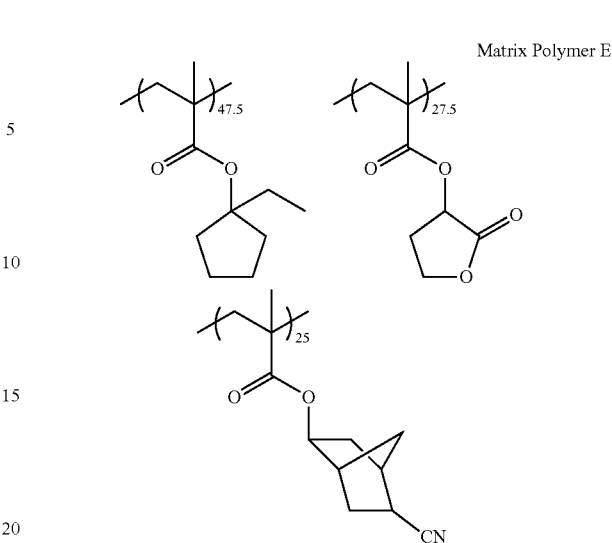

Matrix Polymer E

Additive Polymer Synthesis

Additive polymers were prepared as described in the examples below:

Example 6

Poly(nBMA) Additive Polymer Synthesis (Additive Polymer A)

13.01 g of n-butyl methacrylate (nBMA) was dissolved in 7 g of THF. The mixture was degassed by bubbling with nitrogen for 20 minutes. A 500 mL flask equipped with a condenser, nitrogen inlet and mechanical stirrer was charged with 8 g of THF and the solution was brought to a temperature of 67° C. 2.11 g of V-601 azo initiator (10.0 mol % with respect to monomers) was dissolved in 2 g of THF and charged into the flask. The monomer solution was fed into the reactor at a rate of 6.29 mL/h. The monomer feeding was carried out for three hours 30 minutes. After monomer feeding was complete, the polymerization mixture was stirred for an additional 30 minutes at 67° C. After four hours polymerization (three hours 30 minutes feeding and 30 minutes stirring), 7 g of THF was added to the reactor and the polymerization mixture was cooled to room temperature. Precipitation was carried out in 0.4 L of cold methanol. After filtration, the polymer was dried in a vacuum oven at 60° C. for 48 hours to give 8.4 g of poly(n-butyl methacrylate) (Mw=12,284 and Mw/Mn=1.79) (Additive Polymer A) as shown in Table 1.

Example 7

Poly(iBMA) Additive Polymer Synthesis (Additive Polymer B)

13.00 g of isobutyl methacrylate (iBMA) was dissolved in 7 g of THF. The mixture was degassed by bubbling with nitrogen for 20 minutes. A 500 mL flask equipped with a condenser, nitrogen inlet and mechanical stirrer was charged with 8 g of THF and the solution was brought to a temperature of 67° C. 2.11 g of V-601 azo initiator (10.0 mol % with respect to monomers) was dissolved in 2 g of THF and charged into the flask. The monomer solution was fed into the reactor at a rate of 6.29 mL/h. The monomer feeding was carried out for three hours 30 minutes. After monomer feeding was complete, the polymerization mixture was stirred for an additional 30 minutes at 67° C. After four hours polymerization (three hours 30 minutes feeding and 30 minutes stirring), 7 g of THF was added to the reactor and the polymerization mixture was cooled to room temperature. Precipitation was carried out in 0.4 L of cold methanol. After filtration, the polymer was dried in a vacuum oven at 60° C. for 48 hours to give 7.8 g of the poly(isobutyl methacrylate) (Mw=8,649 and Mw/Mn=1.62) (Additive Polymer B) as shown in Table 1.

Commercial Poly(nBMA) Polymers

Additional poly(n-butyl methacrylate) polymers (Additive Polymers C, D, E, and F), from Polymer Source Inc. (Dorval, Canada), were obtained for use in formulating photoresist compositions, as shown in Table 1.

TABLE 1

| Example | Additive Polymer | Mw | Mw/Mn |
|---------|------------------|-------|-------|
| 1 | A | 12284 | 1.79 |
| 2 | B | 8649 | 1.62 |
| — | C | 10812 | 1.06 |
| — | D | 16350 | 1.09 |
| — | E | 24150 | 1.15 |
| — | F | 54500 | 1.09 |

Photoresist Composition Preparation

Photoresist compositions were prepared as described in the examples below:

Comparative Example 1

4.087 g of Matrix Polymer A formed as described in Example 6 was dissolved in 28.58 g of PGMEA, 19.053 g of cyclohexanone, and 47.58 g of methyl-2-hydroxyisobutyrate. To this mixture was added 0.568 g of "PAG A" described below, 0.071 g of 1-(tert-butoxycarbonyl)-4-hydroxypiperidine quencher and 0.007 g of POLYFOX® PF-656 surfactant (Omnova Solutions Inc.). The resulting mixture was rolled on a roller for six hours and then filtered through a Teflon filter having a 0.2 micron pore size.

PAG A

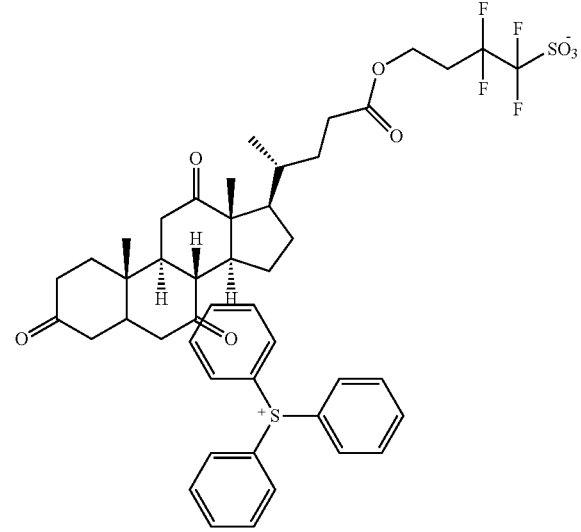

Comparative Examples 2-7 and Examples 8-20

Photoresist compositions were prepared in the same manner described in Comparative Example 1 using the materials and contents shown in Table 2.

TABLE 2

| Example | Matrix Polymer | Additive Polymer | PAG | Quencher | Surfactant | Solvent A | Solvent B | Solvent C |
|---------|---------------|------------------|-----|----------|-----------|-----------|-----------|-----------|
| Comp. 1 | A (4.087) | — | A (0.568) | 0.071 | 0.007 | 28.58 | 19.053 | 47.58 |
| 8 | A (4.040) | A (0.047) | A (0.568) | 0.071 | 0.007 | 28.58 | 19.053 | 47.58 |
| 9 | A (3.992) | A (0.095) | A (0.568) | 0.071 | 0.007 | 28.58 | 19.053 | 47.58 |
| 10 | A (3.945) | A (0.142) | A (0.568) | 0.071 | 0.007 | 28.58 | 19.053 | 47.58 |
| 11 | A (3.898) | A (0.189) | A (0.568) | 0.071 | 0.007 | 28.58 | 19.053 | 47.58 |
| 12 | A (3.945) | B (0.142) | A (0.568) | 0.071 | 0.007 | 28.58 | 19.053 | 47.58 |
| Comp. 2 | B (4.096) | — | A (0.568) | 0.062 | 0.007 | 28.58 | 19.053 | 47.634 |
| 13 | B (4.025) | A (0.071) | A (0.568) | 0.062 | 0.007 | 28.58 | 19.053 | 47.634 |
| 14 | B (3.954) | A (0.142) | A (0.568) | 0.062 | 0.007 | 28.58 | 19.053 | 47.634 |
| 15 | B (3.883) | A (0.213) | A (0.568) | 0.062 | 0.007 | 28.58 | 19.053 | 47.634 |
| 16 | B (3.940) | A (0.142) | A (0.663) | 0.076 | 0.007 | 28.58 | 19.053 | 47.634 |
| 17 | B (3.926) | A (0.142) | A (0.757) | 0.09 | 0.007 | 28.58 | 19.053 | 47.634 |
| Comp. 3 | B (4.380) | — | B (0.331) | 0.014 | 0.007 | 28.58 | 19.053 | 47.634 |
| 18 | B (4.238) | A (0.142) | B (0.331) | 0.014 | 0.007 | 28.58 | 19.053 | 47.634 |
| Comp. 4 | B (3.147) | — | B (0.331) | 0.014 | 0.007 | 28.98 | 19.32 | 48.3 |
| 19 | B (3.045) | A (0.102) | B (0.238) | 0.01 | 0.005 | 28.98 | 19.32 | 48.3 |
| 20 | B (3.045) | B (0.102) | B (0.238) | 0.01 | 0.005 | 28.98 | 19.32 | 48.3 |
| 21 | B (3.045) | C (0.102) | B (0.238) | 0.01 | 0.005 | 28.98 | 19.32 | 48.3 |
| 22 | B (3.045) | D (0.102) | B (0.238) | 0.01 | 0.005 | 28.98 | 19.32 | 48.3 |
| 23 | B (3.045) | E (0.102) | B (0.238) | 0.01 | 0.005 | 28.98 | 19.32 | 48.3 |
| 24 | B (3.045) | F (0.102) | B (0.238) | 0.01 | 0.005 | 28.98 | 19.32 | 48.3 |
| Comp. 5 | C (3.147) | — | B (0.331) | 0.014 | 0.007 | 28.98 | 19.32 | 48.3 |
| 25 | C (3.045) | A (0.102) | B (0.238) | 0.01 | 0.005 | 28.98 | 19.32 | 48.3 |
| Comp. 6 | D (3.147) | — | B (0.331) | 0.014 | 0.007 | 28.98 | 19.32 | 48.3 |
| 26 | D (3.045) | A (0.102) | B (0.238) | 0.01 | 0.005 | 28.98 | 19.32 | 48.3 |
| Comp. 7 | E (3.147) | — | B (0.331) | 0.014 | 0.007 | 28.98 | 19.32 | 48.3 |
| 27 | E (3.045) | A (0.102) | B (0.238) | 0.01 | 0.005 | 28.98 | 19.32 | 48.3 |

PAG B: triphenylsulfonium 1-((3-hydroxyadamantyl)methoxycarbonyl) difluoromethanesulfonate;
Quencher: 1-(tert-butoxycarbonyl)-4-hydroxypiperidine;
Surfactant: POLYFOX ® PF-656 (Omnova Solutions Inc.);
Solvent A: propylene glycol monomethyl ether acetate;
Solvent B: cyclohexanone;
Solvent C: methyl-2-hydroxyisobutyrate.
All contents in grams.

Lithographic Evaluation

Various photoresist compositions were processed and evaluated by dry or immersion lithography as described in the examples below.

Dry Lithographic Evaluation of Comparative Examples 1-3 and Examples 8-18

Dry lithographic evaluations were carried out on 200 mm silicon wafers using a TEL CleanTrack ACT 8 linked to an ASML/1100 scanner with a maximum numerical aperture (NA) of 0.75. Silicon wafers were spin-coated with AR™77 bottom-antireflective coating (BARC) material (Rohm and Haas Electronic Materials) and baked for 60 seconds at 205° C. to yield a film thickness of 840 Å. Photoresist formulations of Comparative Examples 1-3 and Examples 8-18 were coated on the BARC-coated wafers and soft-baked at 100° C. for 60 seconds on a TEL CleanTrack ACT 8 coater/developer to provide a resist layer thickness of 1500 Å.

The photoresist-coated wafers were then exposed through a mask having post patterns for contact hole formation using 0.75 NA and an annular illumination condition with 0.89 outer sigma and 0.64 inner sigma. The exposure dose was 60 mJ/cm$^2$ (Comp. Example 1, Examples 8-12), 52 mJ/cm$^2$ (Comp. Example 2, Examples 13-17) or 37.52 mJ/cm$^2$ (Comp. Example 3, Example 18). The exposed wafers were post-exposure baked at a temperature of 100° C. (Comp. Examples 1-2, Examples 8-17) or 95° C. (Comp. Example 3, Example 18) for 60 seconds and then developed using 2-heptanone for 25 seconds on a TEL CleanTrack ACT 8 coater/developer. Critical dimensions (CD) were measured on a Hitachi 59380 CD SEM at various mask CD and pitches.

It was found that when a matrix polymer was used with no additive polymer in the comparative examples, the printed contact hole patterns included regions in which patterns should have been printed but were absent (i.e., "missing contact holes"). In addition, the printed contact holes were generally irregular in shape (i.e., non-circular) and of poor uniformity. The patterns resulting from the examples in accordance with the invention which included particular additive polymers in addition to the matrix polymer, were significantly improved in terms of missing contact hole patterns, shape and CD uniformity.

Immersion Lithographic Evaluation of Comparative Examples 4-7 and Examples 19-27

300 mm silicon wafers were spin-coated with AR™40A antireflectant (Rohm and Haas Electronic Materials) to form a first bottom antireflective coating (BARC) on a TEL CLEAN TRACK™ LITHIUS™ i+ coater/developer. The wafer was baked for 60 seconds at 215° C., yielding a first BARC film thickness of 840 Å. A second BARC layer was next coated over the first BARC using AR™124 antireflectant (Rohm and Haas Electronic Materials), and was baked at 205° C. for 60 seconds to generate a 200 Å top BARC layer. Photoresist formulations were then coated on the dual BARC-coated wafers and soft-baked (SB) at 100° C. for 60 seconds on a TEL CLEAN TRACK™ LITHIUS™ i+ coater/developer to provide a resist layer thickness of 1000 Å. Photoresist layers made from the comparative (additive polymer-free) compositions were coated with a layer of OC™2000 topcoat material (Rohm and Haas Electronic Materials) before exposure to prevent photoresist components from leaching into the immersion fluid. Photoresist layers made from compositions of the invention (including the additive polymer) were processed without a topcoat layer.

The photoresist-coated wafers were exposed through a mask having post patterns on an ASML TWINSCAN™ XT:1900i immersion scanner with a maximum NA of 1.35 and using diffractive optical elements. Three exposure conditions were used for each resist composition. Annular illumination, 1.35 NA, 0.96 outer sigma, 0.69 inner sigma and XY polarization and (ii) C-Quad 20 illumination, 1.35 NA, 0.988 outer sigma, 0.9 inner sigma and XY polarization each involved a single exposure to print contact holes. The third exposure condition involved double exposure of line/space patterns in a perpendicular direction to print contact hole images. The first exposure was carried out using a dipole illumination with 1.35 NA, 0.97 outer sigma, 0.82 inner sigma and X polarization. Immediately after the first exposure step, the wafers were exposed again using a different mask with a dipole illumination with 1.35 NA, 0.97 outer sigma, 0.82 inner sigma and Y polarization. The exposed wafers were post-exposure baked at 90° C. for 60 seconds and then developed using 2-heptanone for 25 seconds on a TEL CLEAN TRACK™ LITHIUS™ i+ coater/developer to give negative tone patterns. Contact hole patterns were obtained with post patterns and trench patterns were obtained with line patterns on the mask. Critical dimensions (CDs) were measured on a Hitachi CG4000 CD SEM at various mask CD and pitches. The photoresist compositions of Examples 19-27 provided better circularity of the formed contact hole patterns than those of Comparative Examples 4-7. It was additionally found that the photoresist compositions of the invention could be used without the need for a topcoat layer.

What is claimed is:

1. A method of forming a photolithographic pattern, comprising:
   (a) providing a substrate comprising one or more layer to be patterned over a surface of the substrate;
   (b) applying a layer of a photoresist composition over the one or more layer to be patterned;
   (c) patternwise exposing the photoresist composition layer to actinic radiation;
   (d) heating the exposed photoresist composition layer in a post-exposure bake process; and
   (e) applying a developer to the photoresist composition layer, wherein unexposed portions of the photoresist layer are removed by the developer, leaving a photoresist pattern over the one or more layer to be pattern;
   wherein the photoresist composition comprises:
      a first polymer which is acid sensitive;
      a second polymer formed from a monomer having the following general formula (I):

(I)

wherein: P is a polymerizable functional group; Z is a spacer unit chosen from optionally substituted linear or branched aliphatic and aromatic hydrocarbons, and combinations thereof, optionally with one or more linking moiety chosen from —O—, —S—, —COO— and CONR$_1$—, wherein R$_1$ is chosen from hydrogen and substituted and unsubstituted C1 to C10 linear, branched and cyclic hydrocarbons; n is an integer from 0 to 5; and R is chosen from substituted and unsubstituted C1 to C20 linear, branched and cyclic hydrocarbons;

wherein the second polymer is acid insensitive and free of fluorine and silicon, and wherein the second polymer has a surface energy lower than a surface energy of the first polymer;
a photoacid generator; and
a solvent.

2. The method of claim 1, wherein P is a polymerizable backbone moiety having the following general structure:

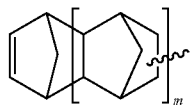

(I-C)

wherein m is an integer from 0 to 3.

3. The method of claim 1, wherein the patternwise exposing is conducted by immersion lithography.

4. The method of claim 1, wherein the patternwise exposing is conducted by immersion lithography.

5. The method of claim 1, wherein R is represented by the formula $C_nH_{2n+1}$, wherein n is an integer from 1 to 6.

6. The method of claim 1, wherein P is a polymerizable functional group having the following general structure:

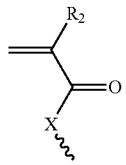

wherein $R_2$ is chosen from hydrogen and substituted and unsubstituted C1 to C3 alkyl; and X is oxygen or is represented by the formula $NR_3$, wherein $R_3$ is chosen from hydrogen and substituted and unsubstituted C1 to C10 linear, branched and cyclic hydrocarbons.

7. The method of claim 6, wherein the second polymer is formed from a monomer chosen from the following monomers:

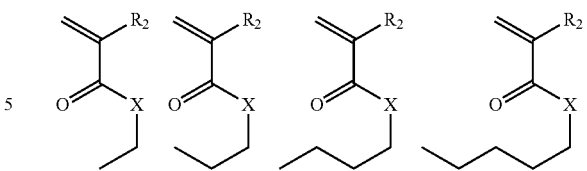

wherein X is oxygen or is represented by the formula $NR_3$, wherein $R_3$ is chosen from hydrogen and substituted and unsubstituted C1 to C10 linear, branched and cyclic hydrocarbons.

8. The method of claim 7, wherein the second polymer is poly(n-butyl methacrylate).

9. The method of claim 1, wherein the second polymer is formed from a monomer chosen from the following monomers:

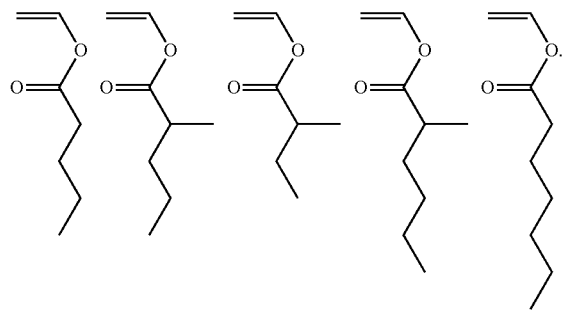

10. The method of claim 1, wherein P is a polymerizable backbone moiety having the following general structure:

wherein $R_4$ is chosen from hydrogen and substituted and unsubstituted C1 to C3 alkyl.

11. The method of claim 1, wherein the first polymer comprises an acid-cleavable group.

* * * * *